United States Patent [19]

Niddam et al.

[11] Patent Number: 5,844,078

[45] Date of Patent: Dec. 1, 1998

[54] PHENYL PEPTIDES, METHOD FOR PREPARING SAME, AND PHARMACEUTICAL COMPOSITIONS CONTAINING SAID PEPTIDES

[75] Inventors: Valérie Niddam, Marseille; Michel Camplo, Isle-sur-Sorgues; Jean-Louis Kraus, Loda-de-Lantosque, all of France

[73] Assignee: Laboratorie Laphal, France

[21] Appl. No.: 793,647

[22] PCT Filed: Jun. 28, 1996

[86] PCT No.: PCT/FR96/01008

§ 371 Date: Feb. 26, 1997

§ 102(e) Date: Feb. 26, 1997

[87] PCT Pub. No.: WO97/01576

PCT Pub. Date: Jan. 16, 1997

[30] Foreign Application Priority Data

Jun. 29, 1995 [FR] France .................................. 95 07817

[51] Int. Cl.⁶ .......................... A61K 38/00; A61K 38/06; A61K 38/08; C07K 7/02

[52] U.S. Cl. .................. 530/328; 514/2; 514/15

[58] Field of Search ..................... 530/328, 334; 514/15, 2

[56] References Cited

U.S. PATENT DOCUMENTS 4,454,065  6/1984  Gilvarg et al. ...................... 260/112.5
5,221,667  6/1993  Kaltenbronn et al. ................... 514/19

FOREIGN PATENT DOCUMENTS 094815  11/1983  European Pat. Off. .
9110679  7/1991  WIPO .

OTHER PUBLICATIONS

Kingsbury–William et al. Int. J. Pept. Protein Res. 27(6), 659–665, Jun. 1986.

Kraus et al. Eur. J. Med. Chem. 27(1), 19–26, Jan. 1992.

*Primary Examiner*—Cecilia J. Tsang
*Assistant Examiner*—Michael Borin
*Attorney, Agent, or Firm*—Bierman, Muserlian and Lucas

[57] ABSTRACT

The present invention relates to synthetic peptides containing as least nine amino acids of formula (I):

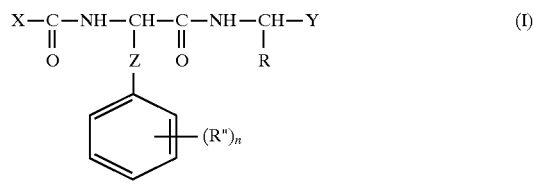

in which X and Y are protected or unprotected amino acid residues, or peptides

R is a linear or branched alkyl radical

R" is one of the following radicals: alkyl, phenyl, halogen, nitro, amino, alkyl amino, alkoxy, trifluoromethyl, trifluoromethoxy, carboxamido or cyano Z is a sulphur, an oxygen, an amino or a sulphoxide and n is equal to 0, 1, 2 or 3. The compounds of formula I are inhibitors of HIV replication by acting as inhibitors of a small aspartyl-protease dimer which specifically cleaves the precursors of a polyprotein coding for the structural proteins and the constitutive enzymes of the HIV virus.

7 Claims, 1 Drawing Sheet

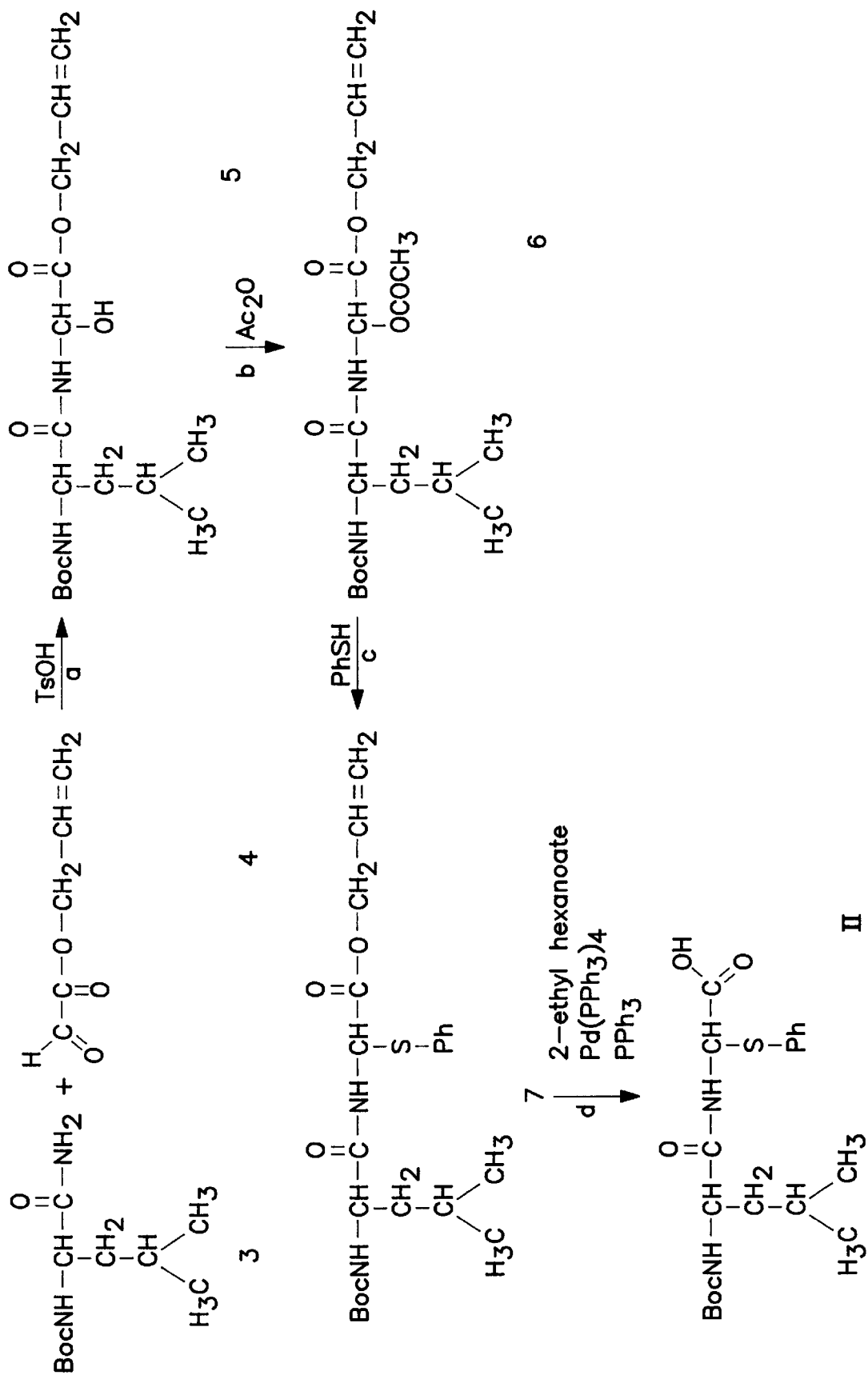

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 9
        ( B ) TYPE: Amino Acid
        ( C ) TOPOLOGY: linear ( i i ) MOLECULE TYPE: peptide ( x i ) SEQUENCE DESCRIPTION: SEQ ID NO:1:

Ile Arg Lys Ile Phe Leu Asp Gly Ile
 1               5

( 2 ) INFORMATION FOR SEQ ID NO:2:

( i ) SEQUENCE CHARACTERISTICS:
        ( A ) LENGTH: 9
        ( B ) TYPE: Amino Acid
        ( C ) TOPOLOGY: linear ( i i ) MOLECULE TYPE: peptide ( i x ) FEATURE:
        ( D ) OTHER INFORMATION: Xaa is a
            phenylalanine isostere as
            defined in the specification.

( x i ) SEQUENCE DESCRIPTION: SEQ ID NO:2:

Ile Arg Lys Ile Xaa Leu Asp Gly Ile
 1               5

( 2 ) INFORMATION FOR SEQ ID NO:3:

```
     ( i ) SEQUENCE CHARACTERISTICS:
           ( A ) LENGTH: 10
           ( B ) TYPE: Amino Acid
           ( C ) TOPOLOGY: linear ( i i ) MOLECULE TYPE: peptide ( x i ) SEQUENCE DESCRIPTION: SEQ ID NO:3:

Ile  Arg  Lys  Ile  Leu  Phe  Leu  Asp  Gly  Ile
 1                    5                        1 0

( 2 ) INFORMATION FOR SEQ ID NO:4:

( i ) SEQUENCE CHARACTERISTICS:
           ( A ) LENGTH: 10
           ( B ) TYPE: Amino Acid
           ( C ) TOPOLOGY: linear ( i i ) MOLECULE TYPE: peptide ( i x ) FEATURE:
           ( D ) OTHER INFORMATION: Xaa is a
                 phenylalanine isostere as defined in the
                 specification. The residue at position 1
                 may or may not be modified with
                 9- fluorenylmethoxycarbonyl (Fmoc).

( x i ) SEQUENCE DESCRIPTION: SEQ ID NO:4:

Ile  Arg  Lys  Ile  Leu  Xaa  Leu  Asp  Gly  Ile
 1                    5                        1 0

( 2 ) INFORMATION FOR SEQ ID NO:5:

( i ) SEQUENCE CHARACTERISTICS:
           ( A ) LENGTH: 10
           ( B ) TYPE: Amino Acid
           ( C ) TOPOLOGY: linear ( i i ) MOLECULE TYPE: peptide ( x i ) SEQUENCE DESCRIPTION: SEQ ID NO:5:

Ile  Arg  Lys  Ile  Leu  Phe  Leu  Asp  Gly  Leu
 1                    5                        1 0
```

PHENYL PEPTIDES, METHOD FOR PREPARING SAME, AND PHARMACEUTICAL COMPOSITIONS CONTAINING SAID PEPTIDES

The present invention relates to the field of organic chemistry and more particularly to that of therapeutic chemistry.

A more particular subject of the invention is new peptides containing phenylalanine (Phe) in which the methylene group has been replaced by an isostere: sulphur, oxygen, amino or sulphoxide.

Specifically, the invention relates to a synthetic peptide containing at least nine amino acids of formula: Ile-Arg-Lys-Ile-Phe-Leu-Asp-Gly-Ile, SEQ ID NO: 1 the methylene group of which carried by the phenylalanine molecule (Phe) has been replaced by an isostere, that is to say that the change in structure according to the invention can be written in the following way:

$$X-\underset{\underset{O}{\|}}{C}-NH-\underset{\underset{\underset{\phantom{|}}{\phantom{|}}}{\overset{|}{CH_2}}}{CH}-\underset{\underset{O}{\|}}{C}-NH-\underset{\underset{R}{|}}{CH}-Y \longrightarrow$$ (I)

(with phenyl ring bearing $(R'')_n$ attached to $CH_2$)

$$X-\underset{\underset{O}{\|}}{C}-NH-\underset{\underset{Z}{|}}{CH}-\underset{\underset{O}{\|}}{C}-NH-\underset{\underset{R}{|}}{CH}-Y$$

(with phenyl ring bearing $(R'')_n$ attached to $Z$)

in which formula X and Y are protected or unprotected amino acid residues, or peptides R is a linear or branched alkyl radical R" is one of the following radicals: alkyl, phenyl, halogen, nitro, amino, alkyl amino, alkoxy, trifluoromethyl, trifluoromethoxy, carboxamido or cyano Z is a sulphur, an oxygen, an amino or a sulphoxide and n is equal to 0, 1, 2 or 3

The Patent WO-A-91 10679 describes renin-inhibiting peptides having an amino acid with a heteroatom in a position at position $P_3$ of the peptide of general formula:

A-X-Y-W-U in which A represents position $P_4$, X position $P_3$, Y position $P_2$ and, W and U positions $P_1$ and $P'_1$.

The preferred compounds which are described in this patent are those for which:

A is IVA (isovaleryl) or BOC (ter-butyloxycarbonyl)

X is —NHCH(SPh)CO—, —NHCH(OPh)CO—, —NHCH(NHPh)CO—, —NHCH(SCH(CH$_3$)$_2$)CO—, —NHCH(SO$_2$CH (CH$_3$)$_2$)CO—, NHCH(NPhCH$_3$)CO—,

Y is HIS (L-histidine) or LEU (L-leucine)

W is CAD (peptidylaminodiols) or STA (4(S)-amino-3 (S)-hydroxy-6-methyl heptanoic acid)

U is MBA (1-hydroxymethyl-2-methyl-butylamine)

with the restriction that if W is CAD, U is absents.

These peptides are renin inhibitors and are used to treat hypertension phenomena, heart failure, glaucoma, hyperaldosteronism.

Renin, just like the HIV protease, is an aspartyl protease and the compounds of Patent WO-A-91 10679 are also used to treat illnesses caused by retroviruses including HTLV -I, -II, -III.

The U.S. Pat. No. 4,454,065 describes pro-drugs having an oligopeptide chain substituted in a position by a chemotherapeutic residue W.

These pro-drugs have the following general formula:

$$P-NHCH(R_1)CO-NHCH(W)CO-Q$$
$$\phantom{P-NHCH(R_1)CO-}2\phantom{NHCH(W)CO}1\phantom{Q}$$

P and Q in particular being able to be amino acids

The glycyl unit 1 is the unit which carries the chemotherapeutic residue W.

One of the preferred compounds of the invention is L-alanyl-L-(α-phenylthio)glycine.

These pro-drugs are used to increase penetration into the infected cells, against which the transported chemotherapeutic residues (W) are active. These chemotherapeutic residues (for example thiophenol) are anti-microbial or anti-parasitic agents.

The reference J. MED. CHEM. (1992), 35(6), 1032-42, describes renin-inhibiting peptides, containing an amino acid with a heteroatom in a position at position $P_2$.

The inhibition of renin can provide an effective treatment for hypertension.

The derivatives described are in particular:

BNMA—NHCH(X)CO—STA—MBA

BNMA (position $P_3$) represents bis (1-naphthylmethyl) acetic acid

STA (position $P_1$) represents 4(S)-amino-3(S)-hydroxy-6-methyl heptanoic acid

MBA (position $P'_1$) represents 2(S)-methylbutylamine

X can for example be: S—C$_6$H$_5$, O—C$_6$H$_5$, N—C$_6$H$_5$ However, the S—, O— and N-aryl derivatives are generally less active than their alkylated analogues.

The reference INT. J. PEPT. PROTEIN RES. (1986), 27(6), 659–665, describes the synthesis of α-thiophenylglycine peptides and more particularly the dipeptide and the two tripeptides which follow:

Ala-α-TPG

Ala-α-TPG-Ala

Ala-Ala-α-TPG

Ala represents alanine

TPG represents thiophenylglycine (—NHCH(SPh)CO—)

These α-substituted glycine peptides are used for transporting the medicament into the microbial cell.

Thus, due to a cleavage produced by peptidase, they deliver the α substituent, that is to say the thiophenol, to the microbial cell.

The compounds according to the invention of formula I can be written more accurately in the following simplified way:

$$\text{Ile}-\text{Arg}-\text{Lys}-\text{Ile}-\text{NH}-\underset{\underset{\underset{Ar}{|}}{\overset{|}{Z}}}{CH}-\text{CONH}-\text{Leu}-\text{Asp}-\text{Gly}-\text{Ile}$$ (I)

SEQ ID NO:2 in which Ar is a non-substituted or substituted phenyl radical.

Z is an isostere as defined previously.

Ile is the amino acid isoleucine

Arg is the amino acid argnine

Lys is the amino acid lysine

Leu is the amino acid leucine

Asp is the amino acid aspartic acid

Gly is the amino acid glycine

In a preferred manner, in this general formula I, Z is sulphur. The compounds of formula I are inhibitors of HIV replication by acting as an inhibitor of a small aspartyl protease dimer which specifically cleaves the precursors of a polyprotein coding for the structural proteins and the constitutive enzymes of the virus (Martin S. A, Recent Advances in the Design of HIV proteinase inhibitors, Antiviral Res. 17 (1992) 265–278).

The compounds of general formula I are prepared using a synthon: [(Boc-Leu)-amino] phenyl Z acetic acid of formula II:

$$\text{Boc NH-CH-CONH-CH-C} \begin{array}{c} \text{O} \\ \text{OH} \end{array} \quad (II)$$

with side chains $CH_2$-CH($CH_3$)$_2$ and Z, Y

Boc = t.butoxycarbonyl in which

Y is a phenyl radical, non-substituted or substituted by one, two or three R" substituents Z is a sulphur, oxygen, amino and sulphoxide isostere which is employed during the peptide synthesis on a template in order to introduce the basic unit on which the present invention rests.

Sheet 1, attached hereto, explains the different stages of the synthesis of synthon II, for which Z is sulphur.

This synthon II is prepared by the following method:

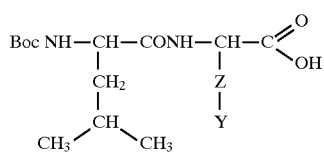

Boc—Leucinamide (3)
+ allyl glyoxylate (4)
→ allyl [(Boc Leu)amino] hydroxyacetate (5)
↓
allyl [(Boc Leu) amino]acetoxy acetate (6)
↓
allyl [(Boc Leu) amino]phenyl sulphanyl acetate (7)
↓
[(Boc Leu) amino]phenyl-sulphanylacetic acid (II)

Boc-Leucinamide (3) was condensed with allyl glyoxalate hydrate (4) to produce the corresponding α-hydroxylated derivative, and thus the allyl ester of Boc-Leu-Gly (5). After acetylation of the hydroxylated function, the resulting ester (6) was displaced by a nucleophilic agent such as a thiophenol in order to obtain compound (7). Elimination of the allyl ester group using the (bis palladium triphenylphosphine) complex in the presence of triphenylphosphine leads to the desired synthon (II) in the form of a diastereoisomer mixture.

It should be noted that the use of other glyoxylic acid esters was found to be less suitable for the condensation on Boc-Leucinamide. In all likelihood, the final deprotection conditions of the ester function lead to the cleavage of the peptide bond. Furthermore, the direct condensation between glyoxylic acid and Boc-Leucine acid proved to be inoperable under the experimental conditions of the test, because the solid phase synthesis (described hereafter) of the peptides (listed in Table 1 hereafter) requires grams of synthon (II).

The same type of synthesis can be used to introduce an —O— or —NH— isostere. The sulphoxide compound is prepared by oxidation using a peroxide of the corresponding sulphurous derivative.

By using the method of solid phase peptide synthesis, according to the operating method described by Nguyen et al (J. Chem. Soc., Perkin Transact. 1 (1987) 1915–1919), starting with this synthon one couples on the different amino acids which constitute the chain of this peptide containing at least nine amino acids. One starts with an MBHA (p.methyl benzhydrylamine) resin or a CM resin (1% cross-linked chloromethylated resin) containing 0.40 mmol of Ile per gram. Coupling was carried out using two equivalents of Boc amino acid and two equivalents of hexafluoro phosphate of [benzotriazolyloxy tris-dimethyl aminophosphonium] (BOP) (Novabiochem). After coupling, deprotection is carried out with 50% trifluoroacetic acid (TFA) at 50% in methylene chloride (DCM). Deprotection of the chain and cleavage of the resin can also be carried out in a single stage, using hydrofluoric acid in the presence of anisole. The peptide resulting from the condensation is purified in an aqueous solution of acetonitrile. The following peptides (given with their number) were successively prepared:

(1) Ile-Arg-Lys-Ile-Leu-Phe-Leu-Asp-Gly-Ile-OH (8) Fmoc-Ile-Arg-Lys-Ile-Leu-(S)Phe-Leu-Asp-Gly-NH$_2$ SEQ ID NO: 3

(9) Ile-Arg-Lys-Ile-Leu-(S)Phe-Leu-Asp-Gly-NH$_2$ SEQ ID NO: 4 amino acids 1–9

(10) Fmoc-Ile-Arg-Lys-Ile-Leu-(S)Phe-Leu-Asp-Gly-Ile-OH SEQ ID NO: 4

(11) Ile-Arg-Lys-Ile-Leu-(S)Phe-Leu-Asp-Gly-Ile-OH SEQ ID NO: 2

(2) BocNH-Leu-(S)PheOH (7) BocNH-Leu-(S)PheOCH$_2$-CH=CH$_2$ in this list and in what follows, the symbol Fmoc means: 9-fluorenylmethoxycarbonyl The preferred sequence, Leu-(S)Phe, can be represented as follows:

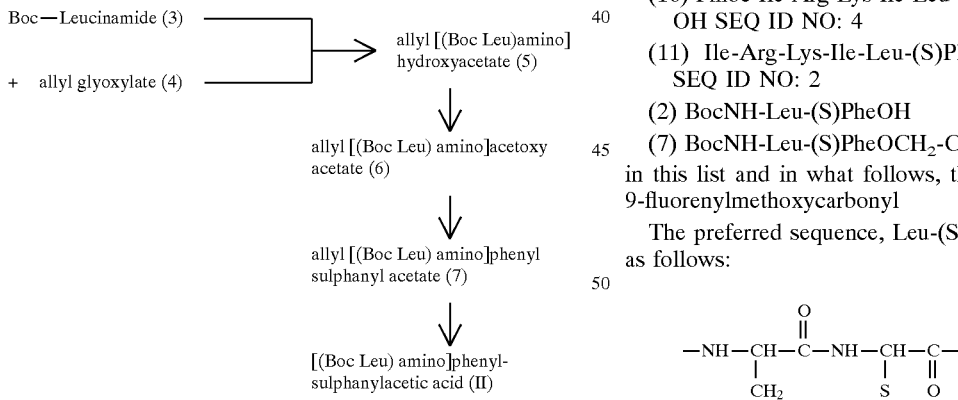

The anti HIV-1 activity of these peptides is represented in Table 1 hereafter.

Also a subject of the invention is the pharmaceutical compositions, intended in particular for the treatment of viral infections caused by the HIV virus, which contain, as active ingredient, at least one compound of general formula I:

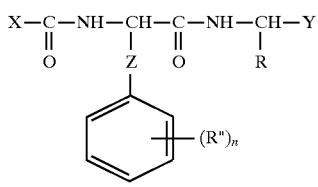

in which X and Y are protected or unprotected amino acid residues, or peptides

R is a linear or branched alkyl radical

R" is one of the following radicals: alkyl, phenyl, halogen, nitro, amino, alkyl amino, alkoxy, trifluoromethyl, trifluoromethoxy, carboxamido or cyano Z is a sulphur, an oxygen, an amino or a sulphoxide and n is equal to 0, 1, 2 or 3 combined with or mixed with a pharmaceutically acceptable, non-toxic, inert excipient or vehicle.

The invention also relates to the pharmaceutical compositions, in particular intended for the treatment of viral infections caused by the HIV virus, which contain, as active ingredient, at least one compound of simplified general formula (I):

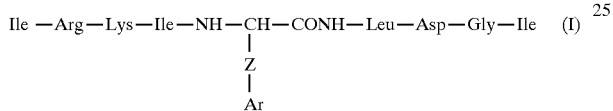

in which Z is sulphur, an oxygen, an amino or a sulphoxide

Ar is a non-substituted or substituted phenyl radical combined with or mixed with a pharmaceutically acceptable, non-toxic, inert excipient or vehicle.

Among the compounds of general formula I, there will preferably be used as active ingredient, that in which Ar is a phenyl radical. Compounds can also be used in which Ar is a phenyl substituted by one, two or three radicals chosen from the group formed by a lower alkyl, a lower alkoxy, a trifluoromethyl, a trifluoromethoxy, a nitro, a carboxamido, a cyano, halogens and a phenyl.

The AIDS virus produces an aspartyl-protease dimer which specifically cleaves the precursors of the polyprotein which codes for the structural proteins and the constitutive enzymes of the virus.

This proteolytic activity is necessary for the production of mature infectious virions and is, consequently, an interesting target for a therapeutic intervention.

Chemists working in therapeutic chemistry have tried to design and synthesize inhibitors of this aspartyl protease enzyme which plays a decisive role.

Most of the laboratories have employed the concept of an analogous transition state. This concept consists of synthesizing the shortest possible peptide substrate, in which the amide bond, normally cleaved, is replaced by a non-hydrolyzable function mimicking a template for a tetrahedral transition state.

Up to now, a large number of templates mimicking the tetrahedral transition state of different states have been put in the presence of the protease of HIV1. They are aminoethylenic isosteres (RICH D. H. et al. J. Med. Chem. 33 (1990) 1285–1288), analogues of statine (HUY K. Y. et al. FASEB J. 5 (1991) 2606–2610—VENAUD S et al. Res. Virol. 143 (1992) 311–319), phosphinic acid isosteres (Grobeiny D. et al. Biochem. Biophys. Res. Commun. 169 (1990) 1111–1116), difluoroketones (SHAM H. L. et al. Biochem. Biophys. Res. Commun. 175 (1991) 914–919), dihydroxyethylene and hydroxyethylamine isosteres (THAISRIVONGS S. et al. J. Med. Chem. 34 (1991) 2344–2356—RICH D. H. et al. J. Med. Chem. 34 (1991) 1222–1225).

The HIV1 protease inhibitors were also designed taking into account the tertiary structure of the enzyme. These compounds can be classified as symmetrical inhibitors or as dimerization inhibitors. In a desire to increase the general scope and the approach of the anti-HIV peptide, the Applicants focused their study on a new concept for an HIV-2 inhibitor based on the following experimental observations:

1. Although after sequential analysis of the sequences of the structural proteins and of the enzymes of infectious mature virions a specific substrate of HIV protease cannot be revealed, certain specificities are however noticed in the cleavage sites produced by these infectious virions.

2. Many peptides which represent known models of proteolytic treatment sites inside the polyproteins of HIV-1 were considered as being accurately cleaved by a synthetic or recombinant protease of HIV-1.

3. Peptides were designed by deduction of the sequencing of the amine or terminal carboxyl functions of the mature HIV-1 proteins. Amongst these, the synthetic peptide Ile-Arg-Lys-Ile-Leu-Phe-Leu-Asp-Gly-Leu SEQ ID NO: 5 was found to be cleaved between the Leu-Phe residue, this cleavage corresponding to the normal cleavage site 727/728 pol (Darke, P. L., Biochem. Biophys. Res. Commun. 1988, 156, 297). Assuming that the replacement of the methylene group of the phenylalanine residue (Phe) in the peptide I by a heteroatom such as sulphur, oxygen, an amino, a sulphoxide, is not going to change the cleavage site between Leu and Phe, it is possible to mention the synthesis and the surprising inhibiting properties vis-à-vis HIV-1, of new isosteres of peptide I. These new peptides contain a glycine substituted in a position by a Z-phenyl in which Z represents sulphur, oxygen, an amino, a sulphoxide. Normally, an α-substituted glycine in which the carbon in α position is linked to a nitrogen, oxygen or sulphur atom is unstable. However, different N-acetylated α-substituted glycines of this type have been described in the literature. Acylation of the amino group leads to stabilization of the molecule by delocalizing the nitrogen electrons on the peptide bond. Instead of using a simple N-acylation to provide the chemical stability of such α-substituted glycines, the Applicants used the Leu-Phe peptide bond so as to mimic peptide I.

The peptides listed in Table 1 were synthesized by the solid phase synthesis technique. This synthesis requires the use of a key synthon (II).

Synthons (2) and (7) were synthesized according to Sheet 1

Synthon (II) was used in the form of a diastereoisomer mixture. Taking into account the unexpected anti-HIV results, it is advantageous to carry out separation by reversed-phase HPLC of the mixture of (2) and/or enantiomeric synthesis of the corresponding peptide in a second study stage.

TEST FOR HIV1 PROTEASE ACTIVITY

The model peptides listed in Table 1 were incubated with HIV-1 protease partially purified using a standard procedure (Billich, J. Biol. Chem. 1988, 263, 17905–17908) and the cleavage products were analyzed by reversed-phase HPLC. Only the peptide I model was cleaved. In a surprising manner, the peptides containing sulphur (2, 7, 8, 9, 10 and 11) were resistant to any proteolytic cleavage under the test conditions. Furthermore, the peptides containing sulphur were added to a test using peptide I as substrate model. It was noted that they were not inhibitors at molar concentrations equal to the substrates (about 2 mM).

ANTI-VIRAL ACTIVITY

The representative compounds listed in Table 1 were also tested for their ability to inhibit infection by HIV1 in cell cultures. The fusogenic effect of HIV1 in the MT4 cell line was determined as described by REY et al. (J. Virol. methods 1987, 16, 239–249) as is shown in Table 1. Some of the new phenylpeptides of the invention were found to be active as inhibitors of HIV replication.

The most active compounds were (9) and (11). These results show that the protection of the N-terminal group by an Fmoc group in compounds (8) or (10) brought about a significant loss of ability to inhibit viral replication in comparison with congeners (9) and (11) whose N-terminal group is free. In addition, the results of the prior art, published by BILLICH et al. (J. Biol. Chem. 263 (1988) 17905–17908), showed that synthetic peptides of 7 to 18 amino acids in length can be used as model inhibiting substrates, for the investigation of protease. It has now been found that the minimum length for peptides containing glycine substituted by a Z-phenyl in a position was 9 or 10 amino acids. According to this viewpoint, the two dipeptides (2) and (7) which contain a -Leu-(S)Phe sequence, proved not to be active as inhibitors of viral replication. With regard to the carbon-containing terminal residue, this preliminary result seems to indicate that the carboxyl group (11) or the carboxamide group (9) may be suitable as inhibitors of the replication of the HIV virus.

This study showed that moderately powerful inhibitors of HIV-1 replication, incorporating a phenylalanine isostere, could be identified. To the knowledge of the Applicants, this is the first time that synthetic peptides which are not substrates or inhibitors of HIV-1 protease may be active against infection by HIV-1 in MT4 cell cultures. This new class of synthetic peptides of HIV protease which is based on the isosteric replacement of a methylene group by a Z isostere atom in a phenylalanine residue positioned on the cleavage site of a synthetic peptide substrate of HIV protease, is of great interest.

The question of the operating mechanism of this new class of compounds seems to be crucial. Tests intended to identify the target in the replication cycle of HIV activated by this new class of compounds must be continued. However, by analyzing the tests carried out to determine the mechanism by which these compounds interfere with the viral replication cycle inside the cell, the results reported here allow it to be assumed that certain peptides which incorporate a Z-phenyl unit are not however active at the level of inhibition of the HIV virus. This lack of activity may be associated with a low membrane permeability of the compounds vis-à-vis MT4 cells, for these new synthetic peptides. In fact, although the compounds like (9) and (11) which have a free terminal ester function showed the greatest anti-HIV effect, peptides (8) and (10) were found to be inactive in infected cultures. It therefore appears that within this new class of synthetic peptides which incorporate the Z-phenyl fraction, the compounds which enter into the infected cell with the greatest efficiency constitute good candidates for studies of the operating mechanism.

To summarize, a new series of inhibitors of the replication of the HIV virus in cell culture which encourages replacement in the phenylalanine residue of a Z atom (Z being defined as previously) has been developed. Although little is yet known about the operating mechanism of these new synthetic compounds, they represent a new approach in the search for new anti-HIV medicaments.

OPERATING METHOD FOR EVALUATION OF THE ANTI-RETROVIRAL PROPERTIES OF NEW PEPTIDE ANALOGUES CONTAINING AN α-SUBSTITUTED GLYCINE RESIDUE

METHOD

Evaluation of the antiviral effect is based on study of the cytopathogenic effect of the HIV 1 virus on the MT4 cell line. The MT4 line originates from T cells isolated from a patient, transformed by the HTLV 1 virus. This line is infected with mycoplasma. The mycoplasma are ubiquitous infectious agents, bacteria living on the surface of MT4 cells as natural hosts. This bacteria, of the order of 300 to 700 nm, is responsible for the great cytopathogenic effect of HIV by the formation of giant cells (fusion by gp 120) called SYNCYTIA. This infection by HIV is observed 4 to 5 days after the infection and is followed by the death of the cells.

This cytopathogenic effect is directly correlated to the infection of the cells by the virus, to its intracellular replication and to the expression of viral antigens by the cells. An inhibition of this effect therefore corresponds to an inhibition of the multiplication of the HIV 1 virus. This lymphoblastoid line infected by HIV 1 can be used for viral production.

The action of the treatment with infectious agents is permanent. In fact, it is present before, during and after the viral infection.

The antiviral perspectives relate essentially to the inhibitors of protease which controls the maturation of proteins and therefore the production of infectious particles, as well as to the inhibitors of the TAT protein which participates in the awakening and the dissemination of the positive regulatory virus of viral transcription and finally to the inhibitors of reverse transcriptase which transforms viral RNA into double-strand DNA, containing the viral message and which is integrated in the provirus form into the DNA of the host cell.

BIOLOGICAL METHODS

INHIBITION IN VITRO OF THE REPLICATION OF THE HIV-1 VIRUS ON THE MT4 CELL LINE

Successive dilutions are carried out in 10% medium in order to be able to culture the MT4 cells for 8 days and to be able to read the formation of the syncytia.
MT4 TEST
before infection $3 \times 10^5$ MT4 cells/100 µl are distributed into a 96-well microplate, centrifuged three times at 2000 rpm and the pellet is preincubated with 100 µl of successive concentrations of the antiviral to be tested, for one hour at 37° under $CO_2$.
infection It is carried out in the microwells by adding a $10^{-3}$ dilution of HIV virus (this dilution of HIV 1 virus is determined so as produce the formation of syncytia in 4 to 5 days). The antiviral is still present during the infection, the final concentration of the virus is then $5 \times 10^{-4}$.

after infection

After incubation for one hour at 37° under $CO_2$, the MT4 cells are washed three times with RPMI 1640 and cultured at the rate of $3 \times 10^5$ cells per 1 ml of each of the concentrations of the compounds to be tested in 24-well plates. The day culturing commences is considered as D0.

On D3 or D4, the MT4 cells are diluted to one third, again in the different concentrations of the antiviral.

Each day, the appearance of syncytia is observed under the microscope in order to see if there is a delay relative to the control HIV-1.

On D8, assay of the reverse transcriptase is carried out. If the cells are not infected, there has therefore been a protection by the tested antiviral.

The $IC_{50}$ dose, that is the concentration of the antiviral which inhibits by 50% the value of the reverse transcriptase of the control HIV 1, was determined.

TABLE 1

Anti HIV-1 activity of the peptides containing the sequence: -Leu-(S)Phe-

| Compound Number | $IC_{50}$ μM | TI ($ID_{50}/IC_{50}$) |
|---|---|---|
| 1 | inactive | — |
| 8 | inactive/toxic | — |
| 9 | 5 ± 2 | 50 |

TABLE 1-continued

Anti HIV-1 activity of the peptides containing the sequence: -Leu-(S)Phe-

| Compound Number | $IC_{50}$ μM | TI ($ID_{50}/IC_{50}$) |
|---|---|---|
| 10 | 100 ± 50 | 10 |
| 11 | 10 ± 5 | 10 |
| 2 | inactive | — |
| 7 | inactive | — |

$IC_{50}$: concentration required to inhibit the formation of syncytia by 50% relative to the control test
TI: therapeutic index: concentration required in order that 50% of MT4 cells are non-infected ($ID_{50}$) relative to the concentration required to inhibit the formation of syncytia by 50% ($IC_{50}$)

Tests carried out on MT4 cells. Viral strain HIV-1 Bru

The foreseeable dosage of the compounds of general formula I will be comprised between 0.1 and 100 mg per unit dose.

Their administration will be carried out by digestive or parenteral route. Their use could be envisaged in the treatment of illnesses associated with the HIV viruses in the form of injectable compositions or in the form of capsules or tablets.

We claim:

1. A peptide having, the formula of which is:

SEQ ID NO:2

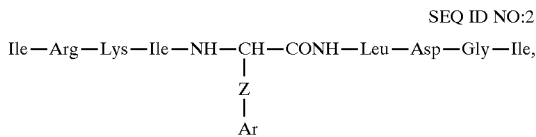

in which Ar is a non-substituted or substituted phenyl radical
Z is sulphur, an oxygen, an amino or a sulphoxide.

2. A peptide according to claim the simplified formula of which is:

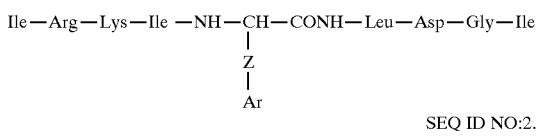

SEQ ID NO:2.

in which Ar is as defined in claim 1.

3. A peptide of the formula

Ile-Arg-Lys-Ile-Leu-(S)Phe-Leu-Asp-Gly-NH$_2$ SEQ ID NO: 4, amino acids 1–9.

4. A peptide of the formula

Ile-Arg-Lys-Ile-Leu-(S)Phe-Leu-Asp-Gly-Ile-OH SEQ ID NO: 4.

5. A composition for the inhibition of replication of HIV virus comprising an inhibitorily effective amount of a compound of claim 1 to prevent replication of HIV virus and an inert pharmaceutical carrier.

6. A composition for the inhibition of replication of HIV virus comprising an inhibitorily effective amount of a compound of claim 3 to prevent replication of HIV virus and an inert pharmaceutical carrier.

7. A composition for the inhibition of replication of HIV virus comprising an inhibitorily effective amount of a compound of claim 4 to prevent replication of HIV virus and an inert pharmaceutical carrier.

* * * * *